United States Patent [19]

Lerman

[11] Patent Number: 4,771,781
[45] Date of Patent: Sep. 20, 1988

[54] CURRENT-BASED DEFIBRILLATING METHOD

[76] Inventor: Bruce B. Lerman, 109 Turtle Creek Rd., Aprt. #10, Charlottesville, Va. 22901

[21] Appl. No.: 915,080

[22] Filed: Oct. 3, 1986

[51] Int. Cl.$^4$ ............................................. A61N 1/36
[52] U.S. Cl. ................................ 128/419 D; 128/734; 128/908
[58] Field of Search ................... 128/419 D, 734, 908

[56] References Cited

U.S. PATENT DOCUMENTS

| 3,782,389 | 1/1974 | Bell | 128/419 D |
| 3,860,009 | 1/1975 | Bell et al. | 128/419 D |
| 3,862,636 | 1/1975 | Bell et al. | 128/419 D |
| 3,886,950 | 6/1975 | Ukkestad et al. | 128/419 D |
| 4,328,808 | 5/1982 | Charbonnier et al. | 128/419 D |
| 4,578,635 | 3/1986 | Mee et al. | 128/419 D |

FOREIGN PATENT DOCUMENTS 0612331  6/1978  U.S.S.R. ............................. 128/908

OTHER PUBLICATIONS

H. G. Goovaerts & M. A. A. M. Meckes, *Accurate Isolated and Microprocessor-Controlled Current Source for a Wide Range of Applications*, Med. & Biol. Eng. & Comput., Jul. 1981, 491–496.

*Current Density and Electrically Induced Ventricular Fibrillation* by Starmer & Whalen, Medical Instrumentation, Jan. '73, pp. 3–7.

Determining Transthoracic Impedance, Delivered Energy, and Peak Current During Defibrillation Episodes, by V. C. Jones, M.S., F. M. Charbonnier, Ph.D, P. Long, B.S., *Medical Instrumentation*, vol. 15, No. 6, Nov.–Dec. 1981.

*Primary Examiner*—William E. Kamm
*Assistant Examiner*—Timothy Keegan
*Attorney, Agent, or Firm*—Walter G. Marple, Jr.

[57] ABSTRACT

Having prospectively ascertained a patient's transthoracic resistance upon application of a low amplitude exploration current via the defibrillator electrodes, the capacitor of the defibrillator is charged sufficiently for delivery of a minimal peak current, e.g., 25 amps, preselected by the operator as appropriate for attaining defibrillation, and the capacitor is discharged to effect the defibrillation.

5 Claims, 2 Drawing Sheets

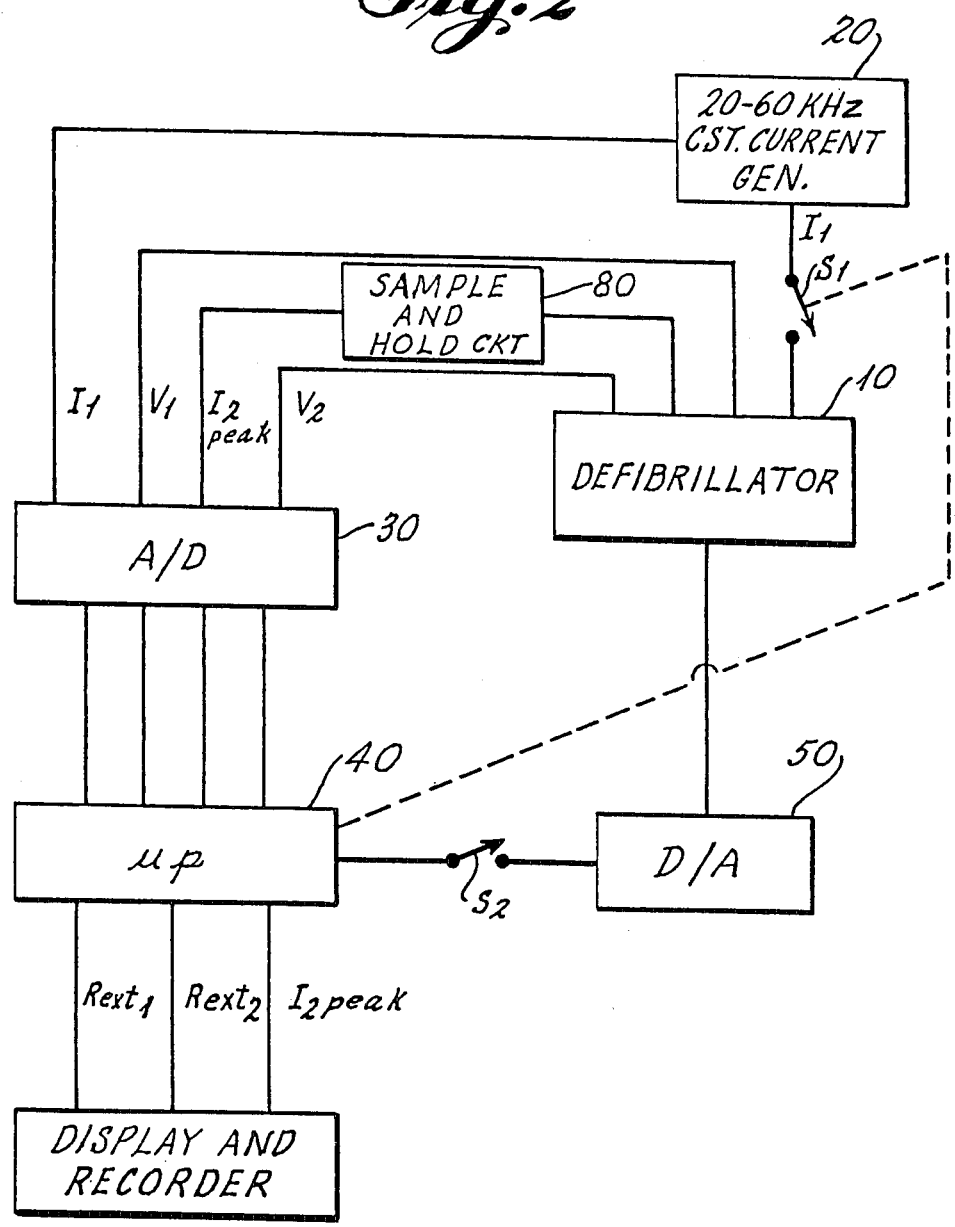

CURRENT-BASED DEFIBRILLATING METHOD

BACKGROUND OF THE INVENTION

Widespread use of DC defibrillators in patients suffering cardiac arrest has greatly increased the rate of successful resuscitation both in and out of hospitals over the past few decades. Defibrillation is applicable to life-threatening cardiac arrests resulting from ventricular fibrillation which occurs because of asynchronous depolarization of cardiac cells. When a sufficient electrical pulse is delivered to the heart from an external defibrillator through a set of paddles (electrodes), all cardiac cells briefly arrest and thereafter synchronous or normal depolarization may once again resume.

The defibrillator equipment presently offered to the medical arts discharges the electrical energy through an RLC circuit which is manually triggered by the physician, and the heretofore standard quantity of the electrical pulse to be delivered has been calibrated in terms of joules of energy. The many studies reported in the medical literature of attempts to determine the optimal electrical strength of the pulse that should be delivered for defibrillation are almost invariably analyzed in terms of joules. Delivery of more than enough electrical energy for defibrillation has been associated with cardiac cell death, yet insufficient energy will not accomplish the desired defibrillation, resulting then in multiple attempts to defibrillate at ever higher energy levels.

Previous recommendations for the "first attempt" defibrillation usually have been based on gross energy levels e.g., 200 joules. In fact, according to the Standards and Guidelines for Cardiopulmonary Resuscitation (CPR) and Emergency Cardiac Care (ECC)—published in JAMA, Vol. 225, pp 2942-2943, 1986, patients in ventricular fibrillation should receive DC countershocks of 200 joules (first shock), 200 joules (second shock), and 360 joules (third shock), as needed.

Selection of energy dose level for threshold defibrillation is believed to be sub-optimal for several reasons. For a given pulse duration, peak current is a better predictor of the defibrillation threshold than delivered energy. In laboratory experiments (on dogs), the inventor hereof has ascertained that defibrillating pulse levels based upon a specified level of peak amperes strongly correlates with threshold defibrillation requirements. Establishment of the defibrillation pulse on the basis of total electrical energy, as has been done by prior workers in the art, does not apply a consistent level of peak current (amperage) because, in humans as well as dogs, transthoracic resistance varies within surprisingly large ranges from one subject to the next. The implication of these findings is that defibrillation dose should be calibrated in units of (or at least based upon) current instead of energy.

An object of this invention is to provide a method and apparatus for automatically providing a preselected threshold level of peak current adequate for defibrillation, wherein the defibrillator capacitor is charged according to the transthoracic resistance of each patient in order to provide the selected peak current.

Additionally, it is an object of the invention to prospectively determine such transthoracic resistance automatically and prior to defibrillation by applying to the patient a low amplitude exploration current via the defibrillator electrodes.

Further objects of the invention and the advantages thereof will become apparent from the description which follows.

RATIONALE OF THE INVENTION

Although it has been customary in the defibrillator art to apply electrical energy as such, i.e., a pulse denominated in joules, some workers in the art have appreciated that delivered current is better than discharged energy as a measurement of a defibrillating threshold, as for example in U.S. Pat. No. 3,862,636, wherein the magnitude of the current delivered to the patient was varied in accordance with the body weight of the patient.

Other recent art has recognized that total energy may not be the most adequate electrical parameter to describe the dose for defibrillation, urging that the peak current level per heart weight or body weight might be the best descriptor of the energy needed to depolarize some critical mass of cells and achieve successful defibrillation, (in the instance of canine hearts at least). See, for example, Armayor et al. "Ventricular Defibrillation Threshholds with Capacitor Discharge", Med. & Biol. Eng. and Comput. 1979, Vol. 17, pp. 435-442. Note is made also of Kerber et al., "Advanced Prediction of Transthoracic Impedance in Human Defibrillation and Cardioversion: Importance of Impedance in Determining the Success of Low Energy Shocks", Circulation, Vol. 70, No. 2, pp. 303-308, 1984. Although their data on minimum current for achieving defibrillation supports the method of the instant invention, Kerber, et al. supra concluded their report with the finding of a wide range of variability in the minimum current required for defibrillation in patients.

Kerber, et al., "Automated Impedance-Based Energy Adjustment for Defibrillation: Experimental Studies", Circulation, Vol. 71, No. 1, January 1985, suggest automatic increases of energy in arbitrary amounts, from an operator-selected energy level, when prospected transthoracic resistance exceeds a threshold mean level based on previously observed patients. U.S. Pat. No. 3,860,009 computes a peak defibrillation current based on energy and transthoracic resistance or body weight.

The gist of the above-noted art is that a need exists for identifying patients with such high thoracic resistance that application of relatively low energy, e.g., 100 joules, defibrillation shock levels are unlikely of success.

The inventor hereof, in U.S. Pat. No. 4,574,810, suggested that such an approach was too gross, and that a superior approach would be to ascertain a threshold level of peak current based on the requirements of each patient, and then to apply whatever electrical energy would result in the desired level of peak current. Further, a resistance measuring system was associated with the defibrillator circuitry and the electrical shock energy administered by the defibrillator was controlled according to measured transthoracic resistance to provide a predetermined amount of peak defibrillation current per calculated ohm of resistance.

In laboratory studies using canines, defibrillation thresholds were determined at two different transthoracic resistances, the resistance being increased by using electrodes of larger contact area or by placing a resistor in series with the thorax and defibrillator. Under the conditions of this study, it was found that threshold defibrillation current was independent of the transthoracic resistance for a given dog while, in contrast, the energy and voltage thresholds showed a large variability. It was found also that a fixed quantity of current would defibrillate each subject, regardless of resistance. Other clinically relevant factors that alter resistance, such as electrode force, number of shocks, electrode gel, and time interval between shocks were found to influence energy requirements while current thresholds remained invariant. Significantly, it was found that the peak defibrillation current related linearly to the delivered energy and the transthoracic resistance, a finding which is particularly relevant since commercially available defibrillators are calibrated for settings of energy rather than peak delivered current. Thus, knowing the transthoracic resistance of the subject and the preselected peak current level to be applied allows determination of the energy setting of commercially available defibrillators in order to deliver the selected peak current level.

To test the hypothesis of peak current being better than energy as a descriptor of the electrical parameter for defibrillation, the inventor hereof conducted a study in which forty (40) patients in ventricular fibrillation were prospectively randomized to receive either DC countershocks according to the above-noted energy-based guidelines or to receive current-based shocks of 25 amps (first shock), 25 amps (second shock), and 40 amps (third shock), by a modified defibrillator, as needed. These patient's were similar with respect to cardiac diagnosis, weight, physical parameters and transthoracic resistance. It was found that energy per shock delivered to patients according to the energy-based guidelines was 75% greater than with the current-based method, while delivering 40% more amps per shock than the current-based method. For instance, 25 amps (initial shock) delivered to a patient having a transthoracic resistance of 70 ohms requires only 90.4 joules of energy, less than half of the energy (200 joules) recommended for the initial shock in the presently accepted guidelines. A first shock efficacy of 67% was realized by use of the current-based method, with 100% of the patient's being defibrillated by the first or second 25 amp shock. Earlier studies indicated that 30 amps (initial shock) defibrillated 75% to 80% of the patients while 40-50 amps defibrillated approximately 100% of the patient's. Of course, some patients may defibrillate with less than 25 amps, but presently there is no way of recognizing these patients beforehand. However, such recognition is apparently not critical since no evidence exists to show significant myocardial damage by application of up to 30 amps.

BRIEF STATEMENT OF THE INVENTION

Briefly stated, the defribrillator of this invention automatically determines transthoracic resistance, and then uses the thus-obtained resistance to calculate (and charge the capacitor to) the level of energy necessary to deliver an amount of peak current preselected by the operator, whereupon the capacitor is discharged to deliver that peak current. This method of defibrillation is applicable to standard defibrillators used for transthoracic defibrillation and to the Automatic Implantable Cardioverter-Defibrillator.

After the defibrillating electrodes are in place on a patient's chest, a low amplitude, sinusoidal pulse (or a rectangular pulse of low frequency, such as 31 kHz) is transmitted through the electrodes and a microprocessor is used to calculate the transthoracic resistance in order that a selected value of peak amperage may be delivered to this subject by the defibrillator. The extreme rapidity of electrical measurements, and the rapid response of electrical circuits to control signals are advantageous, since ventricular fibrillation is of life threatening urgency and brooks no delay.

The selected peak defibrillation current to be applied to the patient and the prospected transthoracic resistance are used to control the charge applied to the capacitor of the defibrillator, so that upon discharge of the capacitor, the selected level of peak current desired for defibrillation will result.

Electrical components and circuitry known to the arts may be employed in practice of the invention. For example, in practice of the invention, standard microprocessors may be adapted to calculate transthoracic resistance from delivered peak exploration current and the electrode-to-electrode voltage developed responsive thereto and to generate an appropriate output signal for controlling charging of the capacitor of the defibrillator so as to generate the selected level of peak defibrillation current.

Suitably, the microprocessor generates a digital signal for visual readout and recording and, in addition, conversion to an analog form for direct control over the charge being placed on the capacitor of the defibrillator.

Desirably, the peak current subsequently delivered to the patient by the defibrillator, and the voltage of the capacitor or across the electrodes are digitized to generate signals which are fed into the microprocessor which, in turn, computes the transthoracic resistance encountered by the defibrillation pulse. The microprocessor then provides appropriate signals for visual readout and recording. For future defibrillation of the same and other patients, it is important to know the degree to which the level of peak current actually delivered by the defibrillator pulse relates to the previously selected peak current level and how transthoracic resistance during defibrillation relates to the patient's resistance measured by the low amplitude exploration current. Given sufficient experiences, a virtually exact predictability for delivered peak current should result, since appropriate adjustments can be made in multiplication factors programmed into the microprocessor.

DISCUSSION OF THE INVENTION

Mention has been made that defibrillation art has concerned itself with measurement of transthoracic resistance and, as might be expected, some suggestions heretofore made to the art are capable of use in practice of this invention, over and above the particular mode hereinafter described. For example, reference is made to "Determining Transthoracic Impedance, Delivered Energy, and Peak Current During Defibrillation Episodes" by Jones et al. in Medical Instrumentation, Vol. 15, No. 6, November–December 1981, pp. 380-382, and, of course, to Kerber et al. supra, as well as Armayor et al. supra.

Important to the practice of this invention, of course, is a consonance of the transthoracic resistance as measured by the low amplitude exploration pulse to the transthoracic resistance under defibrillation pulse circumstances. In this connection, it is noted that Kerber, et al. reported that their predicted resistance correlated very well with defibrillation pulse resistance, and such correlation resulted when practice of this invention advanced from animal model results obtained in the genesis of this invention to clinical studies involving forty humans, (only such being available as of the date hereof).

It is noteworthy that in the relatively few human patients on which resistance measurements have been made by the inventor hereof, the same relatively wide variation in transthoracic resistance person-to-person heretofore reported in the literature has been found to exist. The mean transthoracic human resistance was 72±21 ohms, with the actual measured values being from 33 to 108 ohms. No linear correlation was found between transthoracic resistance and body weight, chest circumference, internal thoracic diameter or chest wall thickness. The transthoracic resistance in humans was not predictable from physical dimensions or body weight.

Through practice of this invention, the physician may apply a defibrillating shock which should be adequate without being excessive, i.e., be close to the threshold. When using defibrillators calibrated for energy level selections, practice of this invention will automatically identify patients at the extremes of the 33-108 ohm range of transthoracic resistance for whom a 100 joule defibrillator shock may be either far too low or excessively high and automatically will cause calculation of the energy level needed to apply a defibrillator shock that delivers the selected level of peak current more appropriate to the patient.

Comparative studies made on canines found that, unlike energy, threshold current requirements are independent of transthoracic impedance and invariant for each dog. Preliminary data also indicate that most humans will be successfully defibrillated with a peak delivered current of 25 amperes.

It has been found also that the transthoracic load of humans is apparently frequency insensitive, remaining constant throughout the frequency spectrum. Further, voltage and current in the defibrillating pulse were virtually in phase throughout all frequencies, indicating that transthoracic impedance is predominately resistive. Therefore, the inventor has used the term "resistance" throughout this discussion when referring to the transthoracic load.

These findings have led to the conceptual framework for practice of this invention, which involves selecting a desired amount of peak delivered current, i.e., 25 amperes, by the operator; prospectively and automatically determining transthoracic resistance of each patient by application of a low energy, high frequency pulse; then automatically charging the defibrillator capacitor to the voltage level sufficient for delivery of the selected level of peak current transthoracically on discharge; and automatically discharging the capacitor for defribrillating upon attaining such voltage level. All of the steps—from measurement through discharge—are performed with the electrodes on the patient.

Additionally, the voltage across the discharge capacitor of the defibrillator, and the peak current supplied by discharge thereof, may be measured so as to compute and display the transthoracic resistance of the patient during defibrillation discharge.

As pointed out by Jones et al., supra, knowledge of the internal circuit parameters peculiar to each defibrillator mode enables normalizing of the peak discharge current. Although not specifically included in the following description of the exemplary embodiment of this invention, normalization for circuit components (internal resistance) in the defibrillator is contemplated, including normalization for add-on internal circuit parameters such as those of the current sensing transformers; and the method and apparatus of the instant invention should be considered as inclusive of performing such normalization whenever desirable. The details of normalization described by Jones et al. supra are incorporated by reference herein as exemplary modes of normalization contemplated herein.

BRIEF DESCRIPTION OF THE DRAWINGS

For further understanding of this invention, reference is made to the attached drawing wherein:

FIG. 2 is a block diagram illustrating a standard defibrillator and the add-on components utilized in practice of the instant invention.

DETAILED DESCRIPTION OF THE INVENTION

Figure 1:
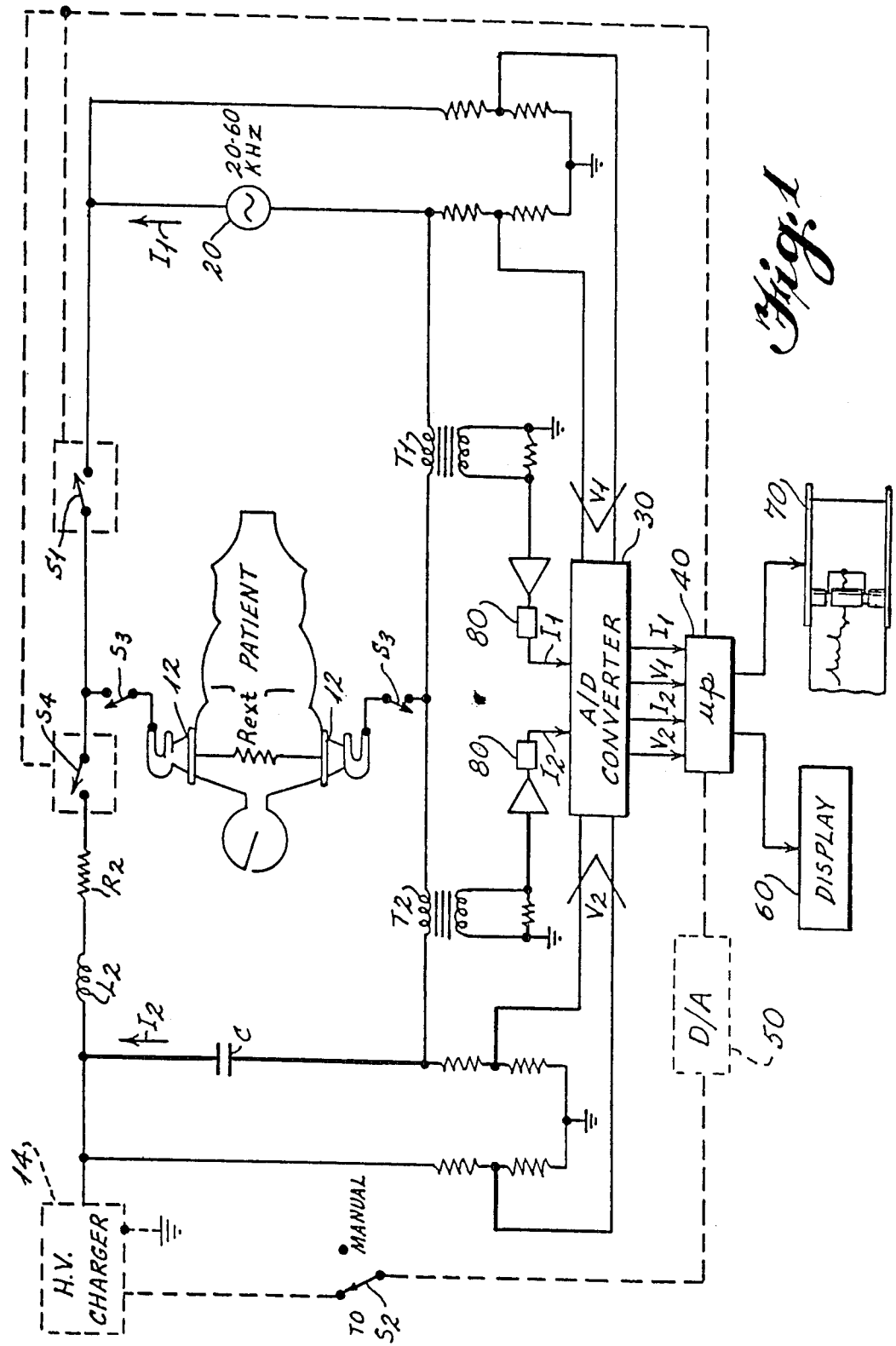
FIG. 1 is a schematic illustration of the invention and the use thereof.

As may be seen in FIG. 1, a conventional defibrillator includes hand-held electrode paddles 12 having switches $S_3$ which must be simultaneously closed in order to apply a defibrillation energy pulse transthoracically to the patient whose heart is in ventricular fibrillation. Closing of switches $S_3$ allows discharge of capacitor C and flow of defibrillating current $I_2$ through a circuit including the transthoracic resistance $R_{ext}$ of the patient. $L_2$ and $R_2$, respectively, represent the internal inductance and resistance parameters of the defibrillator. Additionally, the standard defibrillator includes a circuit for charging capacitor C, such indicated as high voltage charging circuit 14 in FIG. 1. FIG. 1 also discloses a current sensing transformer $T_2$ and an appropriate voltage divider so that the transthoracic resistance $R_{ext}$ may be computed as the quotient of the voltage $V_2$ across capacitor C divided by the peak defibrillating current $I_2$. As may be seen in FIG. 1, A/D converter 30 and microprocessor 40 are used to facilitate calculation of transthoracic resistance and delivered energy during such defibrillation, much as suggested by Jones et al. supra.

According to practice of the invention, the operator will select a desired peak current to be delivered during defibrillation. The microprocessor will then ensure charging of the capacitor to a voltage sufficient to deliver the selected peak current, with this capacitor voltage being dependent on both the selected peak current and prospectively determined transthoracic resistance. A low amplitude (approximately 0.1 milliamp) constant current generator 20 provides a pulse of current at some fixed frequency in the range of 20/60 kHz, as an exploration current $I_1$ passed through paddles 12 via the patient's thorax prior to discharge of capacitor C. A response voltage $V_1$ is developed across paddles 12 appropriately proportional to the product of the transthoracic resistance $R_{ext}$ and the applied current $I_1$. Sensing current $I_1$ via transformer $T_1$ and measuring the response voltage $V_1$, allows a calculated transthoracic resistance $R_{ext1}$ to be obtained by passing the sensed current and voltage through A/D converter 30 then to a microprocessor 40 in which the calculation is performed. Since transthoracic load is predominantly resistive, it may be appreciated that the computed or calculated transthoracic resistance $R_{ext1}$ may then be used, along with the selected peak current to compute the voltage to which the capacitor (C) is charged in order to deliver a preselected quantity of peak current to the patient.

With switch $S_2$ set to AUTO (for automatic) microprocessor 40 controls switches $S_1$ and $S_4$ and high voltage charger 14 such that, upon placing the paddles 12 upon the chest of the patient and depressing switches $S_3$, switch $S_1$ will be closed to apply the exploration current $I_1$ across the patient's chest. Prior to, during, or after measurement of transthoracic resistance, high voltage charger 14 commences to charge capacitor C. After calculating $R_{ext1}$, microprocessor 40, directly or indirectly, opens switch 1 and immediately controls the amount of voltage to which capacitor C is charged so that it will deliver to the patient the preselected (by the operator) peak defibrillating current $I_2$. Upon capacitor C being charged to a voltage sufficient to provide the preselected level of peak current $I_2$, microprocessor 40, directly or indirectly, will (automatically) close switch $S_4$ for consequent defibrillation of the patient. The operator may wish sometimes to apply standard defibrillator operation, i.e., setting of a particular energy level, e.g., in joules, for some particular patient and such is permitted by setting switch $S_2$ to manual.

A display 60 and recording device 70 allow display and recordation of important defibrillation parameters such as: the transthoracic resistance $R_{ext\ 1}$ calculated from the exploration current $I_1$; the transthoracic resistance $R_{ext\ 2}$ computed during defibrillation of the patient; the measured level of peak defibrillating current $I_2$ delivered and the delivered energy.

FIG. 2 is a block diagram generally illustrating the add-on components used with the standard defibrillator 10 for practice of the present invention. Like numerals have been used for like components throughout the drawings.

Just as 200 joules has been used heretofore as an experience—determined energy level for initial defibrillator shock, approximately 25 amperes of peak defibrillation current has been preselected in practice of this invention. This value is based upon limited human patient experience and some change up or down therein may be required with increased human patient experience. As a practical matter, it is proposed that the operator will be able to select from 1–50 peak amperes.

The concept of delivering an optimal peak level of defibrillating current is important to practice of this invention. Analysis of the data available to the inventor thereof has indicated that the critical threshold level correlates with peak current and not energy and that transthoracic resistance correlates with the level of energy necessary to deliver a preselected peak current. Thus, for patients of high transthoracic resistance, defibrillating with 100 joules may apply too low a level of peak defibrillating current. Alternatively, guideline recommended energy levels of 200 joules can provide unnecessarily high peak currents to patients of low transthoracic resistance. Application of some fixed level of peak current to all patients would be an improvement for eliminating current variation patient-to-patient.

I claim:

1. A method of defibrillating the heart of a patient in ventricular fibrillation, and comprising the steps of:
   basing said defibrillating on peak current level to be applied to the heart of the patient;
   selecting a particular value of said peak current level suitable for said defibrillating;
   applying a low amplitude exploration current, from electrodes forming part of a defibrillator, to the chest of said patient and sensing a response voltage developed across said electrodes in response to said exploration current;
   Calculating an explored transthoracic resistance from said exploration current and response voltage; and
   charging a defibrillating capacitor of said defibrillator, based on said particular value of said peak current level selected and according to said explored transthoracic resistance, sufficiently to create a capacitor discharge voltage generative of said particular value of said peak current level, and thereafter discharging said defibrillating capacitor in order to apply said particular value of said peak current level to said patient for defibrillating.

2. A method as in claim 1, and further comprising the steps of:
   calculating actual transthoracic resistance from delivered peak defibrillating current and capacitor discharge voltage; and
   displaying values of peak defibrillation current, delivered energy, and said explored and actual transthoracic resistance.

3. A method as in claim 1, and further comprising the step of:
   providing said defibrillator with operator controls calibrated according to current in order to effect selection of said particular value of said peak current level.

4. A method as in claim 1, wherein said particular value of said peak current level is in a range of about 20–40 amps.

5. A method as in claim 4, wherein said particular value of said peak current level is about 25 amps.

* * * * *